United States Patent
Mercier et al.

(10) Patent No.: US 6,890,519 B2
(45) Date of Patent: May 10, 2005

(54) SILICONE OIL/COSOLVENT SYSTEM CONCENTRATED IN ACTIVE LIPOSOLUBLE COSMETIC SUBSTANCE(S), CORRESPONDING COSMETIC EMULSION AND FORMULATION

(75) Inventors: Jean-Michel Mercier, Gouvieux (FR); Jean-Marc Ricca, Singapour (SG); Nadia Martin, Lyons (FR)

(73) Assignee: Rhodia Chimie, Boulogne Billancourt (FR)

( * ) Notice: Subject to any disclaimer, the term of this patent is extended or adjusted under 35 U.S.C. 154(b) by 127 days.

(21) Appl. No.: 10/239,307

(22) PCT Filed: Mar. 20, 2001

(86) PCT No.: PCT/FR01/00831

§ 371 (c)(1),
(2), (4) Date: Nov. 26, 2002

(87) PCT Pub. No.: WO01/70177

PCT Pub. Date: Sep. 27, 2001

(65) Prior Publication Data

US 2003/0219394 A1 Nov. 27, 2003

(30) Foreign Application Priority Data

Mar. 22, 2000 (FR) .............................................. 00 03677

(51) Int. Cl.⁷ ................................................. A61K 7/00
(52) U.S. Cl. ........................ 424/59; 424/63; 424/70.11; 424/195.17; 424/401; 424/725
(58) Field of Search .................................. 524/284, 588; 424/401, 59, 63, 70, 195.17, 725; 514/159, 167

(56) References Cited

U.S. PATENT DOCUMENTS

| | | | | |
|---|---|---|---|---|
| 3,392,040 A | * | 7/1968 | Kass | ...................... 106/287.13 |
| 5,068,099 A | | 11/1991 | Sramek | |
| 5,122,519 A | * | 6/1992 | Ritter | ......................... 514/152 |
| 5,298,236 A | | 3/1994 | Newcomer et al. | |
| 5,738,841 A | * | 4/1998 | Mellul et al. | ................. 424/59 |
| 6,039,935 A | * | 3/2000 | Mohammadi | ................ 424/59 |
| 6,432,912 B1 | * | 8/2002 | Rodelet | ........................ 512/1 |

FOREIGN PATENT DOCUMENTS

| | | |
|---|---|---|
| EP | 0 152 953 | 8/1985 |
| EP | 0 437 216 | 7/1991 |
| EP | 0 576 748 | 1/1994 |

* cited by examiner

*Primary Examiner*—Margaret G. Moore
*Assistant Examiner*—Marc S. Zimmer
(74) *Attorney, Agent, or Firm*—Burns, Doane, Swecker & Mathis, L.L.P.

(57) ABSTRACT

The invention concerns a silicone oil/cosolvent/active substance(s) system, characterized in that it comprises in solubilized form at least 25 wt. % relative to silicone weight of at least an active substance fat soluble and naturally non-soluble in said silicone.

18 Claims, No Drawings

SILICONE OIL/COSOLVENT SYSTEM CONCENTRATED IN ACTIVE LIPOSOLUBLE COSMETIC SUBSTANCE(S), CORRESPONDING COSMETIC EMULSION AND FORMULATION

The present invention relates to a concentrate of active materials in a silicone derivative, to the corresponding emulsion and to their respective uses in cosmetics formulations.

For the purposes of the invention, the expression "cosmetic formulation" means any cosmetic product or preparation of the type described in Annex I ("Illustrative list by category of cosmetic products") of European Directive No. 76/768/EEC of 25 Jul. 1976, known as the Cosmetics Directive.

In general, cosmetic compositions are formulated in the form of a large number of product types intended to be applied either to the hair, such as mousses, gels (in particular for styling), conditioners, formulations for styling or for making the hair easier to comb and/or disentangle, and rinsing formulations, or to the skin, such as hand and body lotions, products for regulating skin moisturization, cleansing milks, make-up-removing compositions, hair-removing products, creams or lotions for protecting against sunlight and ultraviolet radiation, care creams, anti-acne preparations, local analgesics, make-up formulations such as mascaras, foundations or nail varnishes, products intended to be applied to the lips or other mucous membranes, sticks, solid compositions such as cleansing soaps, and other formulations of the same type.

Most cosmetic or dermatological compositions are in a thickened liquid form of gel or cream type. This type of presentation, which is suitable for consumers, usually provides formulators with practical concerns: making the product easier to take from its packaging without any significant loss, limiting the diffusion of the product to the local zone of treatment, being able to distribute the product uniformly over the local zone of treatment and being able to use it in amounts that are sufficient to obtain the desired cosmetic or dermatological effect.

This objective is fundamental for formulations such as care, hygiene or make-up products which need to be distributed homogeneously over the local area to be treated, as well as hair compositions which need to spread and be distributed uniformly along the keratin fibres.

Silicone derivatives most particularly constitute vehicles of choice for conveying and/or delivering a certain number of cosmetic or pharmaceutical active products across the skin and/or keratin fibres. Their permeability to gas transfers, in particular to water vapour, their "induced amphipathic" nature with an area localization, combined with their harmlessness in particular explain their success in the cosmetics field.

However, the encapsulation of cosmetic active agents in formulations of this type can raise difficulties in certain cases. The cosmetic active agents can be, on the one hand, difficult to incorporate into the formulation, especially for reasons of insolubility, and can be, on the other hand, unstable therein and/or incompatible with other ingredients. This instability is generally reflected by emulsion-demixing or crystallization phenomena in the cosmetic formulation.

The solution generally adopted to prevent the manifestation of these adverse secondary phenomena consists in limiting the amount of active agents in the said formulations.

The object of the present invention is, precisely, to propose a silicone/co-solvent system which advantageously allows the encapsulation of up to 100% by weight of liposoluble organic active materials relative to the weight of silicone. This silicone/co-solvent system is particularly advantageous for preparing cosmetic emulsions and/or more generally cosmetic formulations with a high content of active materials.

Advantageously, the corresponding cosmetic emulsions and/or formulations have satisfactory stability and are not subject to the demixing and/or crystallization phenomena mentioned above.

A first aspect of the invention thus relates to a silicone/co-solvent/active material(s) system, characterized in that it comprises, in a dissolved form, at least 25% by weight, relative to the weight of silicone, of at least one liposoluble active material which is naturally insoluble in the said silicone.

The inventors have demonstrated, unexpectedly, that it is possible, by virtue of the use of a suitable co-solvent, to incorporate, in an efficient and stable manner, large amounts of cosmetic active materials into a silicone derivative and, via this system, into cosmetic emulsions and/or formulations. The systems claimed can thus advantageously contain up to 100% by weight of active materials.

The silicones which can be used in the context of the present invention are preferably silicone oils or gums and more particularly non-volatile oils.

With reference to the three-dimensional solubility space, which solvents and all organic molecules occupy, and which is defined by C. M. Hansen in "The three dimensional solubility parameters" J. Paint Technol. 39, 105 (1967), it is found to be particularly advantageous according to the invention to use silicones which have a $\delta_D$ of less than about 15, a $\delta_P$ of less than about 1 and a $\delta_H$ of less than about 5, i.e. values that are not naturally suited to the dissolution of active materials and in particular highly polar active materials; $\delta_D$, $\delta_P$ and $\delta_H$ represent the partial solubility parameters linked, respectively, to the London dispersion forces, the Keesom polarity forces and the hydrogen bonding forces, given that these partial parameters are the components of the overall solubility parameter $\delta$, known as the Hildebrand solubility parameter, which is associated with the cohesion per unit volume of the molecule.

In addition, the silicones in accordance with the invention preferably have a viscosity of greater than 300 mPa.s, preferably greater than 10,000 mPa.s and more preferably greater than 100,000 mPa.s.

Silicone oils said to be of high viscosity have a viscosity of greater than 1000 mPa.s, for example greater than 3000 mPa.s, preferably greater than 5000 mPa.s or up to 500,000 mPa.s. Silicones of low viscosity are defined as having a viscosity of less than 1000 mPa.s and preferably between 1 and 1000 mPa.s, for example between 20 and 1000 mPa.s.

In the context of the invention and unless otherwise specified, the viscosity values are the dynamic viscosity values measured at 25° C. using a Brookfield viscometer according to the indications of AFNOR standard NFT 76102.

More particularly, the silicones used according to the invention can consist totally or partially of units of formula:

$R'_{3-a}R_a SiO_{1/2}$ (unit M) and/or $R_2SiO$ (unit D) in which formulae:

a is an integer from 0 to 3 the radicals R are identical or different and represent:

a saturated or unsaturated aliphatic hydrocarbon-based group containing from 1 to 10 carbon atoms;

an aromatic hydrocarbon-based group containing from 6 to 13 carbon atoms;

a polar organic group linked to the silicon via an Si—C or Si—O—C bond;

a hydrogen atom:

the radicals R' are identical or different and represent an OH group an alkoxy or alkenyloxy group containing from 1 to 10 carbon atoms;

an aryloxy group containing from 6 to 13 carbon atoms;

an acyloxy group containing from 2 to 13 carbon atoms;

a ketiminoxy group containing from 3 to 8 carbon atoms;

an amino-functional or amido-functional group containing from 1 to 6 carbon atoms, linked to the silicon via an Si—N bond;

Preferably, at least 80% of the radicals R in the said oils represent a methyl group.

These silicones can optionally comprise preferably 5% of units of formula T or Q:

$RSiO_{3/2}$ (unit T) and/or $SiO_2$ (unit Q) in which formula R has the definition given above.

As examples of aliphatic or aromatic hydrocarbon-based radicals R, mention may be made of the following groups:

alkyl, preferably optionally, halogenated $C_1$–$C_{10}$ alkyl, such as methyl, ethyl, octyl or trifluoropropyl;

alkoxyalkylene, preferably of $C_2$–$C_{10}$, better still of $C_2$–$C_6$, such as —$CH_2$—$CH_2$—O—$CH_3$;

alkenyls, preferably $C_2$–$C_{10}$ alkenyl, such as vinyl, allyl, hexenyl, decenyl or decadienyl;

alkenyloxyalkylene such as —$(CH_2)_3$—O—$CH_2$—CH=$CH_2$, or alkenyloxyalkoxyalkyl such as —$(CH_2)_3$—$OCH_2$—$CH_2$—O—CH=$CH_2$ in which the alkyl portions are preferably $C_1$–$C_{10}$ and the alkenyl portions are preferably $C_2$–$C_{10}$;

aryls, preferably of $C_6$–$C_{13}$, such as phenyl.

As examples of polar organic groups R, mention may be made of the following groups:

hydroxy-functional groups such as alkyl groups substituted with one or more hydroxyl or di(hydroxyalkyl) amino groups and optionally interrupted with one or more divalent hydroxyalkylamino groups. The term "alkyl" means a hydrocarbon-based chain preferably of $C_1$–$C_{10}$, better still of $C_1$–$C_6$; examples of these groups are —$(CH_2)_3$—OH; —$(CH_2)_4N(CH_2CH_2OH)_2$; —$(CH_2)_3N(CH_2CH_2OH)$—$CH_2$—$CH_2$—$N(CH_2CH_2OH)_2$;

amino-functional groups such as alkyl substituted with one or more amino or aminoalkylamino groups, in which alkyl is as defined above; examples of these are —$(CH_2)_3$—$NH_2$; $(CH_2)_3$—NH—$(CH_2)_2NH_2$;

amido-functional groups such as alkyl substituted with one or more acylamino groups and optionally interrupted with one or more divalent alkyl-CO—N< groups, in which alkyl is as defined above and acyl represents alkylcarbonyl; an example is the —$(CH_2)_3$—$N(COCH_3)$—$(CH_2)_2NH(COCH_3)$ group;

carboxy-functional groups such as carboxyalkyl optionally interrupted with one or more oxygen or sulphur atoms, in which alkyl is as defined above; an example is the —$CH_2$—$CH_2$—S—$CH_2$—COOH group.

As examples of radicals R', mention may be made of the following groups:

alkoxy, preferably of $C_1$–$C_{10}$, better still of $C_1$–$C_6$, such as methoxy, ethoxy or octyloxy;

alkenyloxy, preferably of $C_2$–$C_{10}$, better still of $C_2$–$C_6$;

aryloxy, preferably of $C_6$–$C_{13}$, such as phenyloxy;

acyloxy in which acyl is preferably $(C_1$–$C_{12})$-alkylcarbonyl, such as acetoxy;

ketiminoxy containing from 3 to 8 carbon atoms, such as ON=$C(CH_3)C_2H_5$;

amino-functional groups such as alkyl or aryl substituted with amino, alkyl preferably being of $C_1$–$C_6$ and aryl denoting a hydrocarbon-based cyclic aromatic group preferably of $C_6$–$C_{13}$, such as phenyl; examples of this are ethylamino and phenylamino;

amido-functional groups such as alkyl-carbonylamino in which alkyl is preferably of $C_1$–$C_6$; an example of this is methylacetamido.

As concrete examples of "units D", mention may be made of: $(CH_3)_2SiO$; $CH_3(CH=CH_2)SiO$; $CH_3(C_6H_5)SiO$; $(C_6H_5)_2SiO$; $CH_3HSiO$; $CH_3(CH_2$—$CH_2$—$CH_2OH)SiO$.

As concrete examples of "units M", mention may be made of: $(CH_3)_3SiO_{1/2}$; $(CH_3)_2(OH)SiO_{1/2}$; $(CH_3)_2(CH=CH_2)SiO_{1/2}$; $(CH_3)_2HSiO_{1/2}$; $(OCH_3)_3SiO_{1/2}$; $[O$—$C(CH_3)=CH_2]_3SiO_{1/2}$; $[ON=C(CH_3)]_3SiO_{1/2}$; $(NH$—$CH_3)_3SiO_{1/2}$; $(NH$—CO—$CH_3)_3SiO_{1/2}$.

As concrete examples of "units T", mention may be made of: $CH_3SiO_{3/2}$; $(CH=CH_2)SiO_{3/2}$; $HSiO_{3/2}$.

When the silicones contain reactive and/or polar radicals R (such as H, OH, vinyl, allyl, hexenyl, aminoalkyl, etc.), these radicals generally represent not more than 5% of the weight and preferably not more than 1% of the weight of silicone.

The polydimethylsiloxane and α,ω-bis(hydroxy)-polydimethylsiloxane oils and gums as well as the polydimethylsiloxane, polyphenylmethylsiloxane and α,ω-bis(hydroxy)polydimethylsiloxane gums are well-known commercial products.

Preference may be given more particularly to α,ω-bis (trimethyl)polydimethylsiloxane oils and gums; α,ω-bis (hydroxy)polydimethylsiloxane oils and gums.

Preferred examples of polydimethylsiloxane oils are those in which the polydimethylsiloxane chain is blocked at its two ends with a $(CH_3)_3SiO_{1/2}$ or $(CH_3)_2(OH)SiO_{1/2}$ group with a dynamic viscosity of 20 mPa.s, of 350 mPa.s, of 750 mPa.s, of 80,000 mPa.s or of 500,000 mPa.s.

As representative silicone oils which are most particularly suitable for the present invention, mention may made in particular of silicones of polydimethylsiloxane (dimethicone) and diphenyl-dimethicone type.

Besides the silicone as defined above, it may be envisaged to incorporate one or more additional oils, preferably chosen from:

mineral oils such as liquid paraffin and liquid petroleum jelly, oils of animal origin such as perhydrosqualene, oils of plant origin such as sweet almond oil, avocado oil, castor oil, olive oil, jojoba oil, sesame oil, groundnut oil, macadamia oil, grape-pip oil, rapeseed oil or coconut oil, synthetic oils such as purcellin oil or isoparaffins, fluoro oils and perfluoro oils.

These additional oils are used in an amount such that they have no effect in terms of polarity compared with the silicone selected.

In accordance with the present invention, the silicone is formulated with a co-solvent.

The co-solvent is chosen so as to allow the solubilization of the active material in the silicone and more specifically so as to compensate for the natural incompatibility manifested in terms of solubility between the silicone and the active material.

For these purposes, the co-solvent is generally chosen such that it has the following Hansen solubility parameters:

$\delta_D$ of London interactions ranging from 11 to 17 $(J/cm^3)^{1/2}$;

$\delta_P$ of Keesom interactions of greater than 2.5 $(J/cm^3)^{1/2}$; and $\delta_H$ of hydrogen bonding ranging from 0 to 23 $(J/cm^3)^{1/2}$.

According to one preferred variant of the invention, this co-solvent is a $C_{10}$ to $C_{20}$ alkyl aliphatic ester and preferably a neopentanoate of a $C_5$ to $C_{12}$ alkyl and preferably of isodecyl.

A system comprising isodecyl neopentanoate and a polydimethylsiloxane with a viscosity equal to 500,000 mPa.s is particularly preferred according to the invention.

A representative system in accordance with the present invention which may be mentioned more particularly is that combining a polydimethylsiloxane of dimethicone or diphenyldimethicone type and isodecyl neopentanoate. The two solvents are preferably used in a weight ratio of isodecyl neopentanoate to polymethylsiloxane ranging from 3:2 to 3:1.

The liposoluble active materials can be solid or liquid. The choice is obviously made as a function of the corresponding cosmetic formulation and its site of application, i.e. on the skin, the hair or the mouth.

When the corresponding cosmetic formulations are intended for oral use, the active material can be chosen from the group consisting of anti-caries compounds, antimicrobial compounds, anti-plaque compounds and flavourings, and mixtures thereof.

The flavourings can be, in particular, essential oils, such as mint oil, lemon oil or aniseed oil, for example. The antimicrobial agents can be chosen from thymol, menthol, triclosan, 4-hexylresorcinol, phenol, eucalyptol, benzoic acid, benzoyl peroxide and butyl paraben, and mixtures thereof.

When the site of application of the cosmetic formulation is the skin, the hair or the nails, the appropriate active materials can be anti-ageing compounds, vitamins, fragrances, antimicrobial agents, bactericides, UV-absorbing agents, anti-acne agents and anti-cellulite agents, as well as mixtures thereof.

As representative anti-ageing agents, mention may be made in particular of retinoids, α- and β-hydroxy acids, their salts and their esters, liposoluble vitamins, ascorbyl palmitate, ceramides, pseudo-ceramides, phospholipids, fatty acids, fatty alcohols, cholesterol and sterols, and mixtures thereof. As preferred fatty acids and alcohols, mention may be made more particularly of those with linear or branched alkyl chains containing from 12 to 20 carbon atoms. It may be, in particular, linoleic acid.

Vitamins which can be formulated are vitamin A and its derivatives, vitamin B2, pantothenic acid, vitamin D and vitamin E.

As representative UV-absorbing materials, mention may be made more particularly of aminobenzoate derivatives of PABA and PARA type, salicylates, cinnamates, anthranilates, dibenzoylmethanes and camphor derivatives, and mixtures thereof.

Anti-cellulite agents which are suitable in particular are isobutylmethylxanthine and theophylline.

Finally, as representative anti-acne agents, mention may be made in particular of resorcinol, resorcinol acetate, benzoyl peroxide, salicylic acid, azelaic acid, long-chain dicarboxylic acids and many natural compounds.

Needless to say, this active material can also be marine extracts, plant extracts, fragrances, dyes or mineral particles in nanoparticulate form such as zinc oxide, titanium oxide or cerium oxides.

It can also be mixtures of the active materials identified above.

The active material(s) selected is (are) dissolved in the silicone or, preferably, in the co-solvent. The second reagent, i.e. the co-solvent or the silicone derivative, is then added and the whole is homogenized with stirring. In fact, the choice of the solubilizing medium is generally made as a function of the desired concentration of active material.

The mixing is generally carried out at room temperature. However, it may, if necessary, be carried out at a higher temperature to facilitate the solubilization provided that this temperature does not risk affecting the properties of the active material.

In a second aspect, the present invention is directed towards the use of a silicone oil/co-solvent system as defined above for the preparation of an emulsion and/or a formulation, preferably a cosmetic emulsion and/or formulation, which is concentrated with liposoluble active material(s) and preferably comprising at least 25% by weight and advantageously up to 100% by weight of active materials relative to the weight of silicone.

A third aspect of the present invention thus relates to emulsions based on the system claimed.

More specifically, the invention covers an emulsion of oil-in-water type comprising a system in accordance with the invention as oily phase.

The preparation of this type of emulsion is known to those skilled in the art. Several methods exist and are described in particular in the following references: Understanding Emulsions (Randy Schueller and. Perry Romanowski Cosmetic & Toiletries Vol. 113 September 98), Formulating Cosmetic Emulsions (Dr Gillian M. Eccleston, Cosmetic & Toiletries Vol. 112 December 97) and Becher's Encyclopedia of Emulsion Technology (P. Becher Ed M. Dekker 1983 and 1985).

The emulsion claimed is stabilized using one or more surfactants.

The nature of the surfactant which can be used for the emulsification is not essential provided it is compatible with cosmetic use.

Thus, nonionic, cationic, anionic or even zwitterionic surfactants can be used.

Examples of anionic surfactants are:

alkyl ester sulphonates of formula R—CH ($SO_3M$)—COOR', in which R represents a $C_8$–$C_{20}$, preferably $C_{10}$–$C_{16}$, alkyl radical, R' represents a $C_1$–$C_6$, preferably $C_1$–$C_3$, alkyl radical and M represents an alkali metal (sodium, potassium or lithium) cation, a substituted or unsubstituted ammonium cation (methyl-, dimethyl-, trimethyl-, tetramethylammonium, dimethylpiperidinium, etc.) or an alkanolamine derivative (monoethanolamine, diethanolamine, triethanolamine, etc.). Mention may be made most particularly of methyl ester sulphonates in which the radical R is $C_{14}$–$C_{16}$;

alkyl sulphates of formula $ROSO_3M$, in which R represents a $C_{10}$–$C_{24}$, preferably $C_{12}$–$C_{20}$ and most particularly $C_{12}$–$C_{18}$, alkyl or hydroxyalkyl radical, M representing a hydrogen atom or a cation of the same definition as above, as well as the ethoxylated (EO) and/or propoxylated (PO) derivatives thereof, containing on average from 0.5 to 6 units and preferably from 0.5 to 3 units of EO and/or PO;

alkylamide sulphates of formula $R_1CONHR'_1OSO_3M$, in which $R_1$ represents a $C_2$–$C_{22}$, preferably $C_6$–$C_{20}$, alkyl radical, $R'_1$ represents a $C_2$–$C_3$ alkyl radical, M representing a hydrogen atom or a cation of the same definition as above, as well as the ethoxylated (EO)

and/or propoxylenated (PO) derivatives thereof, containing on average from 0.5 to 60 EO and/or PO units;

salts of saturated or unsaturated $C_8$–$C_{24}$, preferably $C_{14}$–$C_{20}$, fatty acids, $C_9$–$C_{20}$ alkylbenzenesulphonates, primary or secondary $C_8$–$C_{22}$ alkyl sulphonates, alkylglycerol sulphonates, the sulphonated polycarboxylic acids described in GB-A-1 082 179, paraffin sulphonates, N-acyl N-alkyltaurates, alkyl phosphates, alkyl isethionates, alkyl succinamates and alkyl sulphosuccinates, sulpho-succinate monoesters or diesters, N-acyl sarcosinates, alkylglycoside sulphates, polyethoxycarboxylates, the cation being an alkali metal (sodium, potassium or lithium), a substituted or unsubstituted ammonium residue (methyl-, dimethyl-, trimethyl-, tetra-methylammonium, dimethylpiperidinium, etc.) or an alkanolamine derivative (monoethanolamine, diethanol-amine, triethanolamine, etc.); and phosphates or alkyl phosphate esters.

Examples of nonionic surfactants are:

polyoxyalkylenated (polyoxyethylenated, polyoxypropylenated or polyoxybutylenated) alkylphenols in which the alkyl substituent is $C_6$–$C_{12}$ and containing from 5 to 25 oxyalkylene units; by way of example, mention may be made of the products Triton X-45, X-114, X-100 or X-102 sold by Rohm & Haas Co.;

glucosamines, glucamides;

glycerolamides derived from N-alkylamines (U.S. Pat. No. 5,223,179 and FR-A-1 585 966);

polyoxyalkylenated $C_8$–$C_{22}$ aliphatic alcohols containing from 1 to 25 oxyalkylene (oxyethylene or oxypropylene) units; by way of example, mention may be made of the products Tergitol 15-S-9, Tergitol 24-L-6 NMW sold by Union Carbide Corp., Neodol 45-99, Neodol 23-65, Neodol 45-7 and Neodol 45-4 sold by Shell Chemical Co., and Kyro EOB sold by The Proctor & Gamble Co.;

products resulting from the condensation of ethylene oxide with a hydrophobic compound resulting from the condensation of propylene oxide with propylene glycol, such as the Pluronid® products sold by BASF;

amine oxides such as $C_{10}$–$C_{18}$ alkyl dimethylamine oxides and $C_8$–$C_{22}$ alkoxy ethyldihydroxy-ethylamine oxides;

the alkylpolyglycosides described in U.S. Pat. No. 4,565, 647 and the polyoxyalkylenated derivatives thereof;

$C_8$–$C_{20}$ fatty acid amides;

ethoxylated fatty acids; and ethoxylated amides, amines and amidoamines;

esters of polyoxyalkylenated or non-polyoxyalkylenated sorbitan with $C_8$–$C_{20}$ fatty acids, such as polyoxyethylenated sorbitan oleates (for example Span® and Tween®);

esters of sucrose with $C_8$–$C_{20}$ fatty acids;

mixtures of esters of sucrose with $C_8$–$C_{20}$ fatty acids and of $C_8$–$C_{20}$ fatty acid mono-, di- and/or triglycerides.

Examples of amphoteric and zwitterionic surfactants are:

those of betaine type, such as betaines, sulpho-betaines, amidoalkylbetaines, alkylsultaines and alkyltrimethylsulphobetaines, the products of condensation of fatty acids and of protein hydrolysates, alkylampho-propionates or -dipropionates, amphoteric derivatives of alkylpolyamines such as Amphionic XL® sold by Rhône Poulenc, Ampholac 7T/X® and Ampholac 7C/X® sold by Berol Nobel, and cocoamphoacetates and cocoamphodiacetates.

Nevertheless, nonionic surfactants are preferred and more particularly nonionic surfactants such as polyoxyalkylenated fatty alcohols containing a linear or branched chain, resulting from the condensation of a fatty alcohol with a $C_2$–$C_4$ alkylene oxide such as ethylene oxide, propylene oxide or butylene oxide. By way of example, mention may be made of ethoxylated isotridecyl alcohol.

More generally, the preferred nonionic surfactants are those whose HLB is between 8 and 16, preferably between 10 and 15 and better still between 12.5 and 15.

The term HLB (hydrophilic-lipophilic balance) denotes the ratio of the hydrophilicity of the polar groups of the surfactant molecules to the hydrophobicity of their lipophilic portion. HLB values are reported in particular in various standard manuals such as the "Handbook of Pharmaceutical Excipients, The Pharmaceutical Press, London, 1994".

The surfactant required to prepare the emulsion is either totally present in the aqueous phase or totally present in the oily phase, or else distributed, in variable proportions, between these two phases.

Generally, the emulsion claimed consists of at least 50% by weight and preferably at least 70% by weight of a system according to the invention.

The emulsion claimed preferably has a droplet size of between 25 nm and 350 µm, advantageously less than 3 µm and more preferably less than 0.3 µm.

A fourth aspect of the present invention relates to a cosmetic formulation comprising at least one emulsion or a system in accordance with the present invention.

Preferably, the cosmetic formulations in accordance with the invention use a vehicle, generally water, or a mixture of several vehicles, present in the said formulations in concentrations of between 0.5 and 99.5% approximately and more preferably between 5 and 90% approximately.

The vehicles that are compatible with the formulations according to the invention comprise, for example, those used in sprays, mousses, tonics, gels, shampoos or rinsing lotions.

Needless to say, the choice of the appropriate vehicle depends on the specific application for which the formulation is intended. A vehicle which is suitable for a formulation intended to remain on the surface on which it has been applied (for example a spray, mousse, lotion, tonic or gel) will not be the appropriate vehicle for a formulation which needs to be rinsed out after use (for example a conditioning shampoo or a rinsing lotion).

The vehicles which can be used may thus be simple or complex and may include a large number of products usually used in cosmetic formulations intended for hair, skin or antisun use.

It may thus be water optionally supplemented with a solubilizing agent to dissolve or disperse the active principles used, such as $C_1$–$C_6$ alcohols and mixtures thereof, in particular ethanol, isopropanol or propylene glycol, and mixtures thereof.

When the cosmetic formulations are in the form of sprays, lotions, tonics, gels or mousses, the preferred solvents comprise water, ethanol, volatile silicone derivatives and mixtures thereof. The solvents used in these mixtures can be miscible or immiscible with each other. The mousses and aerosol sprays can also use any propellant capable of generating the products in the form of fine, uniform sprays or mousses. Examples which may be mentioned are dimethyl ether, propane, n-butane and isobutane.

In parallel with the vehicles identified above, the cosmetic formulations according to the invention can contain surfactants, used to disperse, dissolve and stabilize various associated compounds. These surfactants can be of anionic, nonionic, cationic, zwitterionic or amphoteric type and are preferably chosen from the surfactants identified above.

As emerges from the text hereinabove, the cosmetic formulations in accordance with the present invention have the main aim of delivering and depositing the formulated active material, for example, onto skin or hair target surfaces. This formulation should thus allow the active material to be deposited onto the surface treated, and the active material should remain there after the formulation is removed by washing and rinsing it off. Since these deposition surfaces are negatively charged, the usual approach for carrying out this deposition consists in combining the active material with cationic compounds and more particularly cationic polymers.

The cationic polymers that are more particularly useful for ensuring this conditioning role are, in particular, polymers of polyquaternium type, such as, for example, polyquaternium-1, polyquaternium-2, polyquaternium-4, polyquaternium-5, polyquaternium-6 (also known as Merquat 100® available from Calgon), polyquaternium-7 (also known as Merquat 550® available from Calgon), polyquaternium-8, polyquaternium-9, polyquaternium-10 (also known as Polymer JR 400®), polyquaternium-11, polyquaternium-12, polyquaternium-13, polyquaternium-14, poly-quaternium-15, polyquaternium-16, polyquaternium-17, polyquaternium-18, polyquaternium-19, poly-quaternium-20, polyquaternium-24, polyquaternium-27, polyquaternium-28, polyquaternium-29 (also known as Kytamer KC® available from Amerchol), polyquaternium-30, polyquaternium-31, poly-quaternium-32, polyquaternium-33, polyquaternium-34, polyquaternium-35, polyquaternium-36, poly-quaternium-37, polyquaternium-37.

Cationic derivatives of polysaccharides, such as cocodimonium hydroxyethyl cellulose, guar hydroxypropyl trimonium chloride, hydroxypropyl guar hydroxypropyl trimonium chloride (Jaguar C 13S® and Jaguar $C_{162}$® sold by Rhodia), trimethylammonium-3 propyl cellulose poly(1,2-oxyethanediyl)-2-hydroxy chloride ether or polyquaternium-10 are also suitable.

The cosmetic formulations can also contain polymers with film-forming properties which can be used to provide a fixing function. These polymers are generally present in concentrations of between 0.01 and 10%, preferably between 0.5 and 5%. They are preferably of the polyvinylpyrrolidone, copolymers of polyvinylpyrrolidone and of methyl methacrylate, copolymer of polyvinylpyrrolidone and of vinyl acetate, polyethylene glycol terephthalate/polyethylene glycol copolymers, sulphonated terephthalic copolyester polymers type.

The cosmetic formulations can also contain polymeric derivatives which exert a protective function, in amounts of about 0.01–10%, preferably about 0.1–5%; by weight, these being derivatives such as cellulose derivatives, polyvinyl esters grafted onto polyalkylene skeletons, polyvinyl alcohols, sulphonated terephthalic copolyester polymers, ethoxylated monoamines or polyamines and ethoxylated amine polymers.

Moisturizers can also be incorporated into the cosmetic formulations. Examples of moisturizers which may be mentioned in particular are glycerol, propylene glycol, urea, collagen, gelatin, and emollients which are generally chosen from alkylmonoglycerides, alkyl-diglycerides, triglycerides such as oils extracted from plants and from vegetables or hydrogenated derivatives thereof, mineral oils or paraffin oils, diols, fatty esters and silicones.

Preserving agents such as p-hydroxybenzoic acid esters, sodium benzoate or any chemical agent which prevents the proliferation of bacteria or of yeasts and used conventionally in cosmetic compositions are generally introduced into these compositions in a pro-portion of from 0.01 to 3% by weight in accordance with annex VII of the cosmetics regulation.

Finally, the cosmetic formulations can also contain viscosity-modifying or gelling polymers such as crosslinked polyacrylates of the Carbopol® type sold by BF Goodrich, anionic acrylic copolymers of the Aculyn® type sold by ISP (International Specialty Products), cellulose derivatives such as hydroxypropylcellulose or carboxymethylcellulose, guars and derivatives thereof, for instance hydroxypropyl guar such as Jaguar HP®, carob, tara gum, cassia gum, xanthan gum such as Rhodicare®, succinoglycans, alginates, carrageenans, chitin derivatives or any other polysaccharide with a texturing function.

The cosmetic formulations according to the invention can be used advantageously in the oral, hair, antisun, bodycare and make-up fields.

The examples given below are presented simply for non-limiting illustration of the present invention.

EXAMPLES 1 TO 5

Preparation of a Concentrate of Cosmetic Active Materials in a Silicone Oil

Isodecyl neopentanoate is used as co-solvent, along with polydimethylsiloxane 5,000,000 silicone oil sold by Rhodia.

The active agent(s) is(are) incorporated beforehand into the co-solvent and the silicone is then homogenized with the resulting mixture.

The amounts of reagents and the nature of the active agents incorporated are presented in Table 1 below.

TABLE 1

|  | Active mixture | Example 1 | Example 2 | Example 3 | Example 4 | Example 5 |
|---|---|---|---|---|---|---|
| Co-solvent | Isodecyl neopentanoate | 55 | 70.5 | 64 | 50 | 58.8 |
| Active materials | Octyl methoxycinnamate | 17.3 | — | 9.3 | — | — |
|  | Butylmethoxydibenzoylmethane | — | 6 | 5.5 | — | — |
|  | Drometrizole trisiloxane | — | — | — | 25 | — |
|  | Triclosan | — | — | — | — | 11.8 |
| Silicone oil | PDMS 500,000 | 27.7 | 23.5 | 21.2 | 25 | 29.4 |
|  | % active agent/silicone | 62.5 | 25.5 | 70 | 100 | 40 |
|  | Co-solvent/silicone ratio | 2:1 | 3:1 | 3:1 | 2:1 | 2:1 |

The degree of incorporation of the active material into the silicone derivative ranges between 25.5% and 100% depending on its nature.

For all the examples, the co-solvent/silicone weight ratio ranges-from 2:1 to 3:1.

EXAMPLES 6 TO 18

Preparation of Emulsions in Accordance with the Invention

The mixture to be emulsified, i.e. a concentrate prepared according to Examples 1 to 5, is dispersed in water in the presence of Laureth 8EO as nonionic surfactant under high shear.

Table 2 below gives the particle sizes and the concentrations after dilution in a water/Laureth sulphate 2EO mixture.

EXAMPLES 19 TO 22

Preparation of Cosmetic Formulations

The encapsulation of UVB and/or UVA screening agent and mixed UVB-UVA screening agent in the silicones facilitates their incorporation, for example, into rinse-out formulations. Furthermore, the joint use of cationic polymer and of these emulsions increases the deposition of the screening agent, for example of the Drometrizole trisiloxane.

TABLE 2

| Emulsion | Active agent | Composition Active agent function | Mixture used | Final % of the mixture in the emulsion | Diameter μm |
|---|---|---|---|---|---|
| Example 6 | octyl methoxycinnamate | UVB screening agent | Example 1 | 73 | 0.74 |
| Example 7 | octyl methoxycinnamate | UVB screening agent | Example 1 | 73 | 0.71 |
| Example 8 | octyl methoxycinnamate | UVB screening agent | Example 1 | 73 | 0.71 |
| Example 9 | butylmethoxydibenzoylmethane | UVA screening agent | Example 2 | 60 | 0.61 |
| Example 10 | butylmethoxydibenzoylmethane | UVA screening agent | Example 2 | 75.8 | 0.64 |
| Example 11 | butylmethoxydibenzoylmethane | UVA screening agent | Example 2 | 75.6 | 0.63 |
| Example 12 | octyl methoxycinnamate/ butylmethoxydibenzoylmethane | UVB screening agent/UVA screening agent mixture | Example 3 | 75.2 | 0.7 |
| Example 13 | octyl methoxycinnamate/ butylmethoxydibenzoylmethane | UVB screening agent/UVA screening agent mixture | Example 3 | 75.2 | 0.65 |
| Example 14 | octyl methoxycinnamate/ butylmethoxydibenzoylmethane | UVB screening agent/UVA screening agent mixture | Example 3 | 75.2 | 0.76 |
| Example 15 | Drometrizole trisiloxane | UVB-UVA screening agent | Example 4 | 60 | 0.62 |
| Example 16 | Drometrizole trisiloxane | UVB-UVA screening agent | Example 4 | 60 | 0.70 |
| Example 17 | Drometrizole trisiloxane | UVB-UVA screening agent | Example 4 | 60 | 0.70 |
| Example 18 | Triclosan | Bactericide | Example 5 | 81.8 | 2 |

The particle sizes are generally in the region of 0.7±0.1 μm.

The emulsions are entirely stable on storage. Thus, for the emulsions (Examples 15 to 17), no change in the particle size over 9 months at room temperature and no recrystallization of the solid active agents are observed.

Finally, taking into account the composition of the mixtures (Examples 1 to 5), the degree of encapsulation of active material in the silicone oil ranges from 25.5% to 100% depending on the active agents.

The incorporation of a non-emulsified mixture (Examples 1 to 5) leads, in a formulation intended for rinsing out, to highly polydispersed particles of 15–20 μm and these coarse sizes are unfavourable for deposition.

Specifically, various formulations were studied, namely LESNa/CAPB and LESNa/CAMA in the presence of cationic polymer.

The results are given in Table 3 below.

TABLE 3

| | Compounds | Function | Example 19 | Example 20 | Example 21 | Example 22 |
|---|---|---|---|---|---|---|
| Water | | solvent | qs 100 | qs 100 | qs 100 | qs 100 |
| Rheozan ® | succinoglycan gum | thickener and stabilizer | 0.3 | 0.3 | 0.3 | 0.3 |
| Jaguar Excel ® | guar hydroxypropyl-triaminonium chloride | conditioner | 0.15 | 0.15 | 0.15 | 0.15 |
| Tegobetaine L7 ® | cocamidopropylbetaine | co-surfactant | — | — | 2.5 | 2.5 |
| Miranol UC32 ® | sodium cocoamphoacetate | co-surfactant | 1.2 | 1.2 | — | — |
| Empicol ESB/3M ® | sodium laureth sulphate | surfactant | 10.8 | 10.8 | 7.5 | 7.5 |
| Emulsion Drometrizole trisiloxane (e.g.: Examples 15 to 17) | | | | 1% screening agent 1% silicone | | 1% screening agent 1% silicone |
| Mixture (e.g.: Example 4) | | | 1% screening agent 1% silicone | | 1% screening agent 1% silicone | |

The pH is adjusted to 6
NB: the percentages are expressed as active agents.

The deposition yields for the Drometrizole trisiloxane (%) as a function of the particle size in the shampoo are given in Table 4 below.

TABLE 4

|  | Particle size in the formulation μm | Deposition yield (%) |
|---|---|---|
| Example 19 | 15 | 8 ± 2 |
| Example 20 | 0.7 | 24 ± 4 |
| Example 21 | 15 | 3 ± 1 |
| Example 22 | 0.7 | 16 ± 3 |

The joint use of an emulsion of screening agent of small particle size and of cationic polymer is favourable for deposition compared with a synthetic mixture.

These emulsions can be used in topical form.

EXAMPLE 23

Two formulations of rinse-out products for skincare intended to impart antisun protection after rinsing with water are prepared.

The two formulation examples given below are two formulations of shower gel type giving an in vitro SPF of 4 after rinsing. The evaluation of the in vitro sun protection factor consists in spreading a given amount of shower gel (2 mg per cm$^2$) onto a support of Bande Transport® type sold by 3M (hypoallergenic micro-perforated adhesive plaster recognized as reproducing the skin relief) according to the recommendations of the European regulation for antisun products marketed after Jan. 1, 1996 suitable for the COLIPA method for in vivo SPF evaluation. The SPF measurements are carried out using an Optometrics SPF 290 Analyse® UV/visible spectrophotometer.

TABLE 5

|  | Formulations | Function | Example 1 | Example 2 |
|---|---|---|---|---|
| Miranol ultra ® L32 | Sodium lauroamphoacetate | co-surfactant | 9.6 | 7.6 |
| Empicol ESB/3M | Sodium laureth sulphate | surfactant | 13 | 10.3 |
|  | Isostearic acid |  | 5 | 4 |
|  | Citric acid |  | 1.6 | 1.3 |
|  | Emulsion: |  |  |  |
|  | dimethicone of viscosity 500,000 mPa · s |  | 2.3 | 2.3 |
|  | isodecyl neopentanoate |  | 6.8 | 6.8 |
|  | *UVA + UVB screening agents |  | 1.6 | 1.6 |
|  | Preserving agent |  | qs | qs |
|  | Distilled water |  | qs 100 | qs 100 |

Note:
pH = 6–6.5
*UVB screening agent: octyl methoxycinnamate
*UVA screening agent: butylmethoxydibenzoylmethane

What is claimed is:

1. An oil-in-water emulsion comprising as an oily phase at least one silicone/co-solvent/active substance(s) system comprising as a solubilized form at least 25% by weight based on the weight of the silicone, of at least one liposoluble active substance which naturally is insoluble in said silicone.

2. The emulsion according to claim 1, wherein the co-solvent has in the solubility medium space of Hansen the following parameters:
   $\delta_D$ London interactions from 11 to 17 $(J/cm^3)^{1/2}$,
   $\delta_P$ Keesom interactions greater than 2,5 $(J/cm^3)^{1/2}$, and
   $\delta_H$ hydrogen bond from 0 to 23 $(J/cm^3)^{1/2}$.

3. The emulsion according to claim 1, wherein the silicone has in the solubility space of Hansen the following parameters:
   $\delta_D$ London interactions lower than 15 $(J/cm^3)^{1/2}$,
   $\delta_P$ Keesom interactions lower than 1 $(J/cm^3)^{1/2}$, and
   $\delta_H$ hydrogen bond lower than 5 $(J/cm^3)^{1/2}$.

4. The emulsion according to claim 1, wherein the silicone has a viscosity greater than 300 mPa.s.

5. The emulsion according to claim 1, which includes at least a silicone which is totally or partially constituted of moieties of formula:

$$R'_{3-a}R_a SiO_{1/2} \text{ and } R_2SiO$$

where:
   a is a integer from 0 to 3
   the radicals R are identical or different and represent:
   an aliphatic saturated on unsaturated hydrocarbon group containing from 1 to 10 atoms of carbon;
   an aromatic hydrocarbon group containing from 6 to 13 atoms of carbon;
   a polar organic group linked to the silicone by a bond Si—C or Si—O—C;
   an hydrogen atom,
   the radicals R', identical or different, represent:
   an hydroxyl group
   an alcoxy or alcenyloxy group having from 1 to 10 atoms of carbon;
   an aryloxy group having from 6 to 13 atoms of carbon;
   an acyloxy group having from 2 to 13 atoms of carbon;
   acetiminoxy group having from 3 to 8 atoms of carbon;
   an amino- or amido-group having from 1 to 6 atoms of carbon, linked to the silicone atom by a bond Si—N.

6. The emulsion according to claim 1, wherein the silicone comprises a silicone like dimethicone or diphenyldimethicone.

7. The emulsion according to claim 1, wherein the co-solvent is an aliphatic ester of a $C_{10}$ to $C_{20}$ alcohol.

8. The emulsion according to claim 1, wherein the co-solvent is a ($C_5$ to $C_{12}$-alkyl) neopentanoate.

9. The emulsion according to claim 1, wherein the co-solvent is isodecyl neopentanoate.

10. The emulsion according to claim 1, comprising isodecyl neopentanoate and a polydimethylsiloxane having a viscosity of 500 000 mPa.s.

11. The emulsion according to claim 10, wherein the co-solvent and the silicone are present in a weight ratio from 3:2 to 3:1.

12. The emulsion according to claim 1, wherein the system comprises from 25 to 100% by weight based on silicone weight of active substance(s).

13. The emulsion according to claim 1, wherein the liposoluble active substance(s) are selected from the group consisting of perfumes, essential oils, fatty acids, color agents, opacity agents, UV-absorbing organic compounds, vitamins, flavanoids, α- and β-hydroxyacids, sea extracts, vegetable extracts, bactericides, and mixtures thereof.

14. The emulsion according to claim 1, stabilized with one or several surfactants.

15. The emulsion according to claim 1, comprising at least 50% by weight of said system.

16. The emulsion according to claim 1, having droplets from 25 nm to 350 μm.

17. Cosmetic formulation comprising at least an emulsion according to claim 1.

18. Cosmetic formulation according to claim 17, further comprising a cationic polymer.

* * * * *